United States Patent [19]
Podesva et al.

[11] 3,953,448

[45] Apr. 27, 1976

[54] PIPERAZINO-ANILIDO COMPOUNDS

[75] Inventors: Ctirad Podesva, Montreal; William T. Scott, Ville de Lery; David W. Henson, LaSalle, all of Canada

[73] Assignee: Delmar Chemicals Limited, Ville LaSalle, Canada

[22] Filed: Dec. 7, 1972

[21] Appl. No.: 311,702

[52] U.S. Cl. .......................... 260/268 BZ; 424/250
[51] Int. Cl.$^2$ ............... C07D 295/10; C07D 295/12
[58] Field of Search ............................. 260/268 BZ

[56] References Cited
UNITED STATES PATENTS

| | | | |
|---|---|---|---|
| 3,267,104 | 8/1966 | Hermans et al. | 260/268 BZ |
| 3,439,035 | 4/1969 | Grisar et al. | 260/268 BZ |

OTHER PUBLICATIONS

Janssen, Pharmaceutica Chemical Abstracts Vol. 64, pp. 12706, 04, (1966).

Alfred Burger, Medicinal Chemistry, 3rd Ed. Part I RS403.88 GR.120 pp. 636–638 (1971).

Alfred Burger, Medicinal Chemistry, 3rd Ed. Part II p. 1588, (1971).

*Primary Examiner*—Alton D. Rollins
*Assistant Examiner*—Jose Tovar
*Attorney, Agent, or Firm*—Christen & Sabol

[57] ABSTRACT

Novel 1,4-disubstituted piperazine compounds and pharmaceutical compositions incorporating such compounds in conjunction with orally, parenterally or rectally administrable pharmaceutically acceptable carriers are disclosed. These compounds have coronary vasodilating properties. Also disclosed are processes for preparing these compounds, and novel intermediate compounds used in such processes.

12 Claims, No Drawings

PIPERAZINO-ANILIDO COMPOUNDS

BACKGROUND OF THE INVENTION

The present invention relates generally to a novel series of chemical compounds, to pharmaceutical compositions containing such compounds and to processes for preparing such compounds in which novel compounds are used as intermediates. More particularly, this invention is primarily concerned with novel 1,4-disubstituted piperazine compounds of the following general formula:

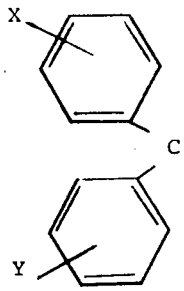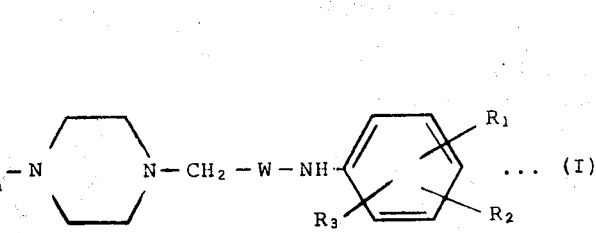

wherein at least one of X and Y represents a halogen atom and the other represents a hydrogen or halogen atom, R₁, R₂ and R₃, which may be the same or different, represent a hydrogen or halogen atom or a lower alkyl or alkoxy group, W represents a carbonyl or lower alkylene group, and m is 1,2 or 3. The invention also contemplates the quaternary ammonium and acid addition salts of these compounds. Representative piperazine compounds encompassed by the foregoing general formula I have been found to be biologically active in that they manifest significant coronary vasodilating properties.

DESCRIPTION OF THE PRIOR ART 1,4-Disubstituted piperazine compounds similar to those of the foregoing general formula I are known, being described, for instance, in U.S. Pat. No. 3,267,104. However, in such prior art compounds, the asymmetric carbon atom always carries a hydrogen atom and there is no description, teaching or suggestion in the prior art that the carbon atom may carry the tertiary hydroxyl group substituent characteristic of the active compounds of this invention. The tertiary hydroxyl group endows the compounds of this invention with advantageous properties compared to the known compounds.

DESCRIPTION OF THE INVENTION a. Novel 1,4-Disubstituted Piperazine Compounds

According to this invention, in one of its composition of matter aspects, there are provided novel 1,4-disubstituted piperazine compounds of the following general formula:

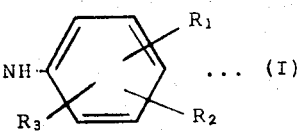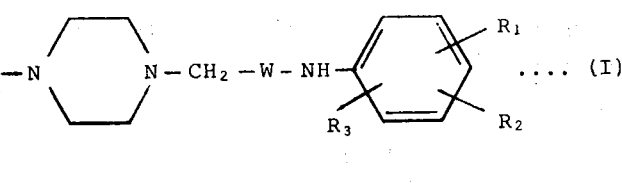

wherein at least one of X and Y represents a halogen atom and the other represents a hydrogen or halogen atom, R₁, R₂ and R₃, which may be the same or different, represent a hydrogen or halogen atom or a lower alkyl or alkoxy group, W represents a carbonyl or a lower alkylene group and m is 1,2 or 3. Quaternary ammonium and acid addition salts of such compounds are also included within the scope of this invention.

The term "lower" as used herein in relation to the alkyl, alkoxy and alkylene groups connotes an alkyl, alkoxy or alkylene group containing no more than six carbon atoms, and preferably no more than three carbon atoms including straight or branched aliphatic chains such as, for example, methyl, ethyl, propyl, isopropyl, butyl, isobutyl, tertbutyl, pentyl, methoxy, ethoxy, propoxy, isopropoxy, butoxy, isobutoxy, tertbutoxy, pentoxy, methylene, ethylene, propylene, isopropylene, butylene, isobutylene, tertbutylene, pentylene and the like.

A preferred class of compounds are those having the following general formula:

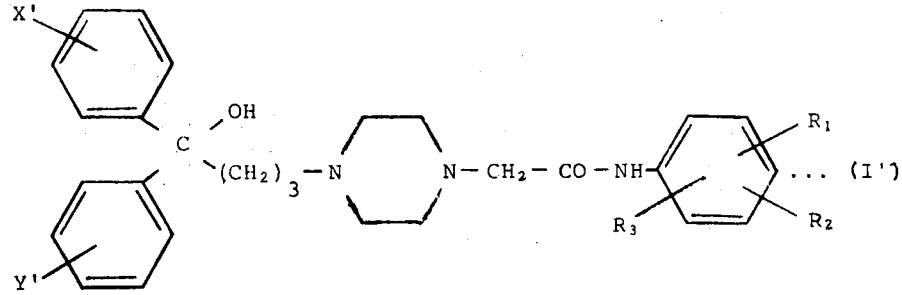

wherein at least one of X' and Y' represents a fluorine atom and the other represents a hydrogen atom or a fluorine atom, and $R_1$, $R_2$ and $R_3$ have the same significance as in formula I hereinbefore. Within this preferred class, compounds of particular note are those in which X' and Y' are both fluorine such as, for example, a 1-[4'-hydroxy-4',4'-bis-(4''-fluorophenyl)]-butyl -4-piperazinoacetyl-2,6-dimethylanilide which has been found to possess significant coronary vasodilating properties when tested pharmacologically by standard, scientifically acceptable procedures in experimental animals such as cats and rabbits, demonstrating potential utility in the treatment of coronary vascular disease.

The free bases of this invention are usually white crystalline solids at room temperature. They are generally relatively insoluble in water and in most organic solvents such as lower alkyl alcohols and esters, acetone and the like. They are, however, soluble in chloroform. These compounds form acid addition salts with strong acids such as, for example, hydrochloric acid, sulfuric acid, perchloric acid and the like. The compounds also form salts with organic acids such as, for example, fumaric, maleic and tartaric acid. Such salts, in general, are soluble in water, methanol and ethanol, but relatively insoluble in benzene, ether, petroleum ether and the like.

b. Novel Processes for Making Compounds of Formula I

The novel substituted piperazine compounds of formula I may be obtained by a number of different processes, the more important of which are summarised in the following reaction schemes.

PROCESS I

This process involves the condensation of the appropriately substituted diphenyl tertiary alcohol in the form of a reactive derivative thereof, with the appropriately substituted piperazino-anilide derivative as illustrated below:

wherein X,Y,$R_1$,$R_2$,$R_3$,W and m have the same significance as hereinbefore and A is a reactive, replaceable group capable, optionally in the presence of a catalyst or initiator for the reaction and under appropriate temperature conditions, of reacting together with the hydrogen atom on the secondary ring nitrogen atom so as to result in direct formation of a C—N bond. Conveniently, the reactive group A is the reactive ester of the corresponding alcohol with a strong inorganic or organic acid such as, for example, hydrochloric, hydrobromic, hydroiodic, sulfuric, methanesulfonic and toluenesulfonic acid.

PROCESS II

In this process, the appropriately substituted diphenyl piperazino compound of the following general formula:

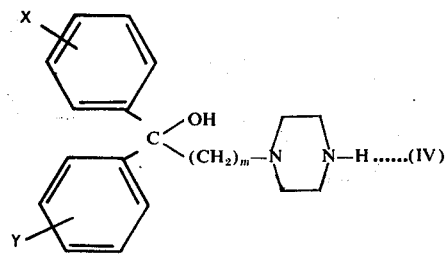

is reacted with a compound of the following general formula:

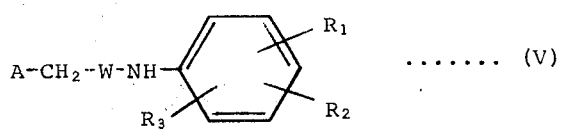

wherein X, Y, $R_1$, $R_2$, $R_3$, W, A and m have the same significance as hereinbefore.

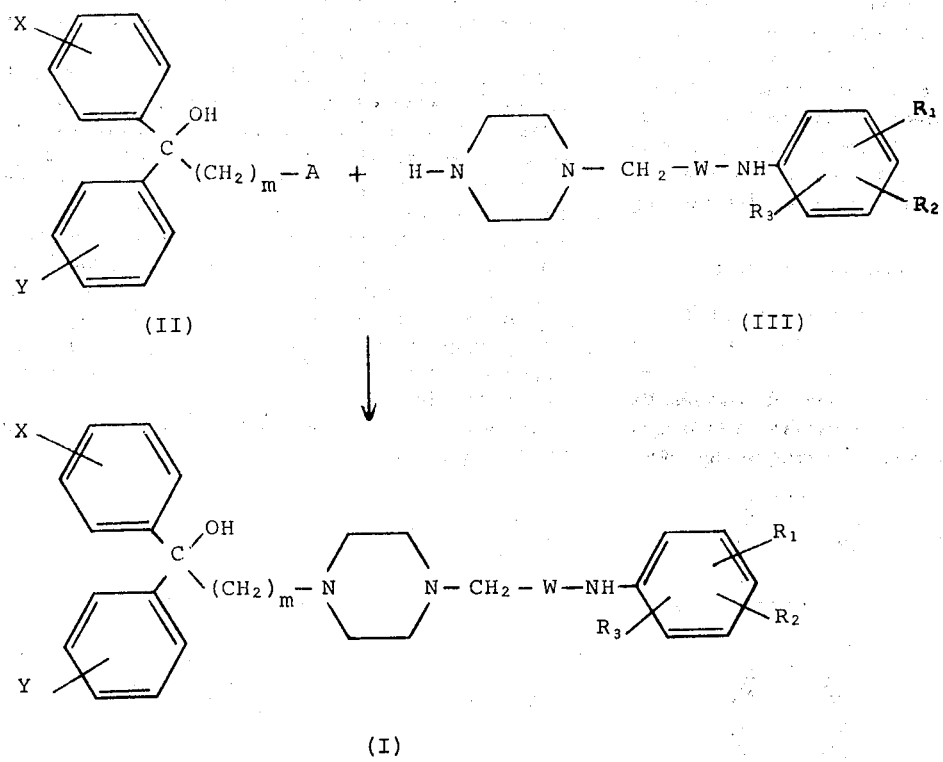

PROCESS III

In this process, which is suitable for making those compounds of formula I in which W is a lower alkylene group, the appropriately substituted diphenyl piperazine compound of the following general formula:

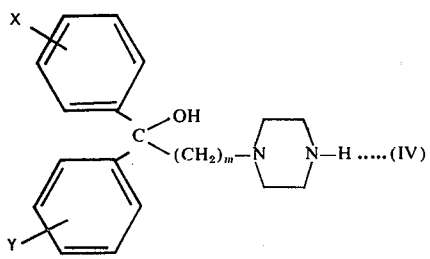

is reacted with a compound of the following general formula:

to yield a compound of the following general formula:

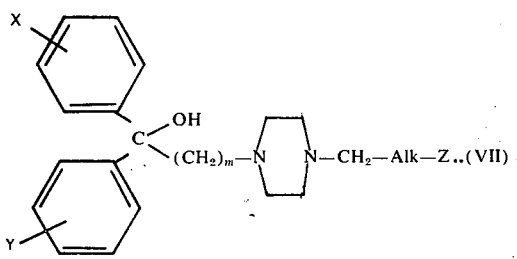

wherein X, Y, A and m have the same significance as hereinbefore, Alk represents a lower alkylene group and Z represents hydroxy or A. In the event Z represents hydroxy, the alcohol is transformed into a reactive derivative, say a reactive ester by treatment with a strong inorganic or organic acid following conventional procedures. With Z in the form of a resulting reactive replacable group, the compound of formula VII is reacted with an anilino compound of the following general formula:

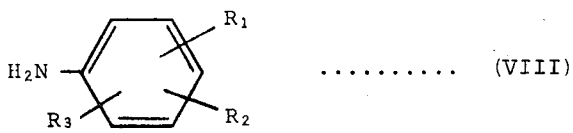

wherein $R_1$, $R_2$, and $R_3$ have the same significance as hereinbefore, to give the desired compound of the general formula I.

The foregoing reactions summarized in Processes I to III hereinbefore are advantageously conducted by heating the reactants together in the presence of a suitable inert organic solvent. Preferably, the reactions are carried out at elevated temperatures, conveniently at the reflux temperature of the particular solvent used. Among suitable solvents, mention may be made of ketones such as, acetone or 4-methyl-2-pentanone; aromatic and aliphatic hydrocarbons, such as, benzene, toluene, xylene or heptane; ethers, such as tetrahydrofuran, dioxane or diethyl ether and esters, such as butyl or ethyl acetate.

Compounds of the general formula I in which W represents carbonyl may be converted into their reduced counterparts, i.e. W represents lower alkylene, by any one of a number of standard reduction procedures such as, for example, by reaction with an excess of a mixed metal hydride, say, lithium aluminum hydride in a suitable inert organic solvent, such as, for example, tetrahydrofuran, dioxane or diethyl ether.

Depending upon the reactants and the conditions employed during the course of the reaction, the novel 1,4-disubstituted piperazine compounds of formula I are obtained either in the form of the free base or as a salt thereof. The salts may be converted into the free bases in the usual manner, for example, by reaction with an alkali such as sodium or potassium hydroxide. The free bases may be converted to acid addition and quaternary ammonium salts by reaction of the free base with the selected acid or alkyl, alkenyl, cycloalkyl, or aralkyl ester. When the compounds are to be used for any non-pharmaceutical application, the toxicity or non-toxicity of the salt is immaterial. When the compounds are to be used as pharmaceuticals they are most conveniently used in the form of water-soluble, non-toxic acid addition or quaternary ammonium salts. The acids which can be used to prepare the preferred non-toxic acid addition salts are those which produce, when combined with the free bases, salts whose anions are relatively innocuous to the animal organism in therapeutic doses of the salts, so that beneficial physiological properties inherent in the free bases are not vitiated by side-effects ascribable to the anions. Appropriate acid addition salts are those derived from mineral acids such as hydrochloric acid, hydrobromic acid, hydriodic acid, nitric acid, sulfuric acid and phosphoric acid; and organic acids such as acetic acid, citric acid, lactic acid, tartaric acid and maleic acid. The quaternary ammonium salts are obtained by the addition of alkyl, alkenyl, cycloalkyl, or aralkyl esters of inorganic acids or organic sulfonic acids to the free base. The alkyl, cycloalkyl, alkenyl or aralkyl esters so used include such compounds as methyl chloride, methyl bromide, methyl iodide, ethyl bromide, propyl chloride, allyl chloride, allyl bromide, dimethyl sulfate, methyl benzenesulfonate, methyl p-toluenesulfonate, benzyl chloride, cyclopentyl bromide, benzyl bromide, and substituted benzyl halides, such as p-chlorobenzyl chloride, p-nitrobenzyl chloride, o-chlorobenzyl chloride, p-methoxybenzyl chloride, and the like.

The acid addition salts are prepared, for example, by dissolving the free base in an aqueous solution containing the appropriate acid and isolating the salt by evaporating the solution, or by reacting the free base and the selected acid in an organic solvent, in which case the salt separates directly or can be obtained by concentration of the solution.

The quaternary ammonium salts are prepared, for example, by mixing the free base and the alkyl, alkenyl, cycloalkyl, or aralkyl ester in an organic solvent. Heating may be used to facilitate the reaction. The quaternary ammonium salt separates directly or can be obtained by concentration of the solution.

c. Reactants and Processes for Making Them

The diphenyl tertiary alcohol compounds of the general formula II hereinbefore may be obtained by a process involving the following steps:

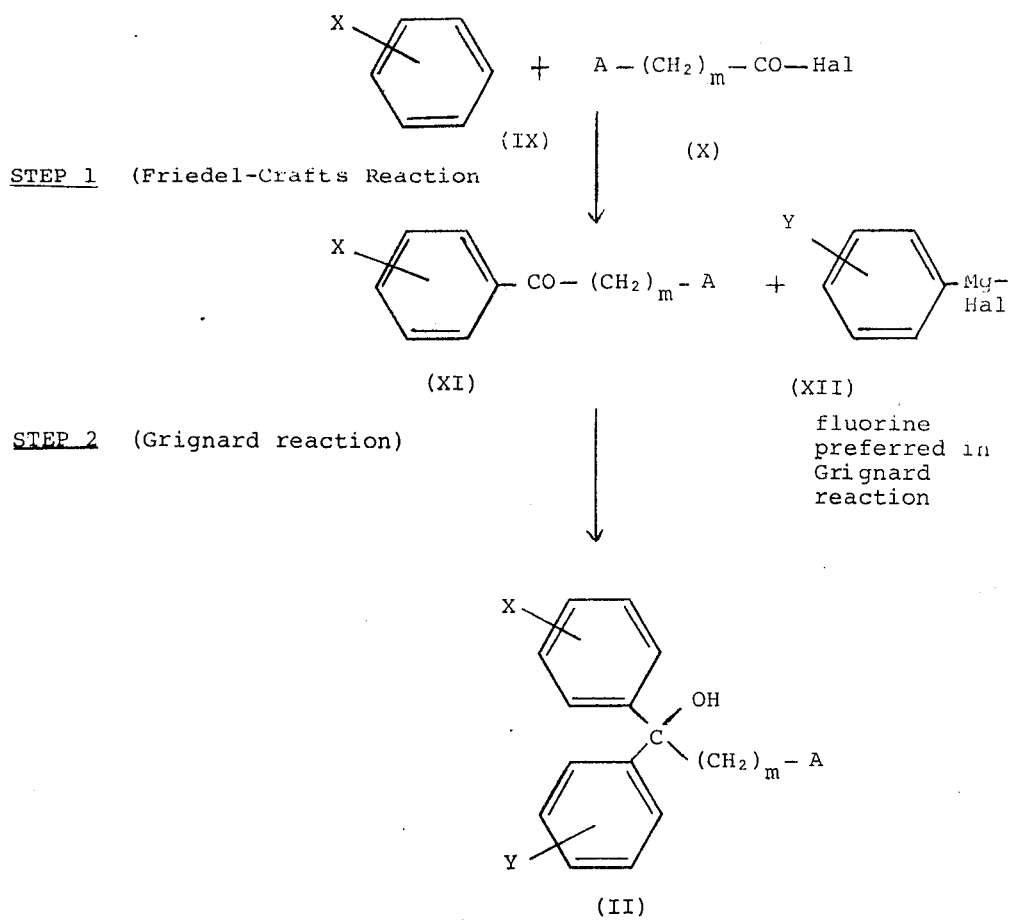

STEP 1 (Friedel-Crafts Reaction)

STEP 2 (Grignard reaction)

fluorine preferred in Grignard reaction

In the foregoing formulae X, Y, $m$ and A have the same significance as hereinbefore and Hal represents a halogen atom. These diphenyl tertiary alcohol compounds are themselves novel and constitute a further composition of matter aspect of this invention. The diphenyl tertiary alcohols may be converted into compounds of the general formula IV by reaction with a piperazino compound as illustrated below:

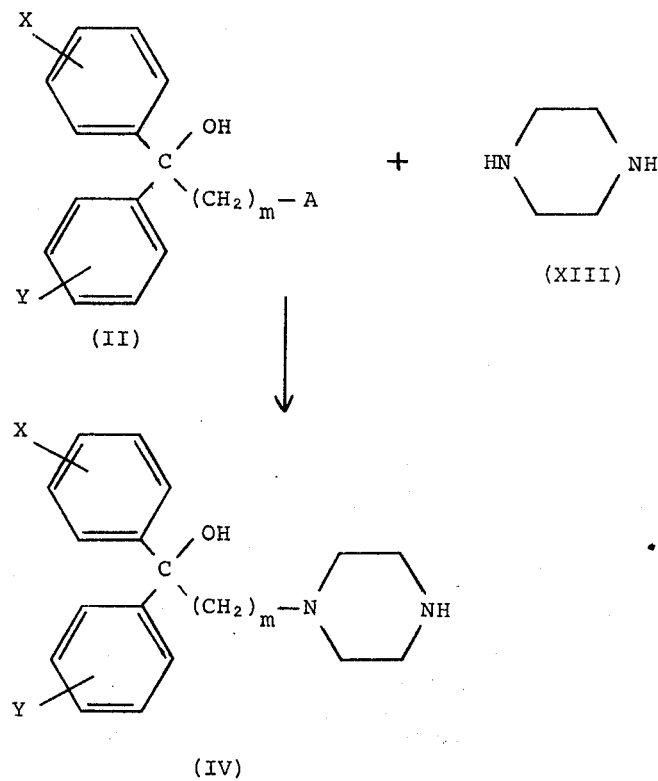

Alternatively, the compounds of formula IV may be obtained by reacting a compound of formula XIII, in which one of the ring nitrogen atoms is blocked by a suitable blocking group such as, for example, a benzyl group with a compound of formula II, and subsequently removing the blocking group. When the blocking group is a benzyl group this may be removed by any convenient debenzylation procedure such as, for example, hydrogen activated by a suitable catalyst, for example, palladium-on-charcoal, in an alcoholic solvent such as methanol or ethanol.

The piperazino-anilide compound of the general formula III obtained by a process involving the following steps:

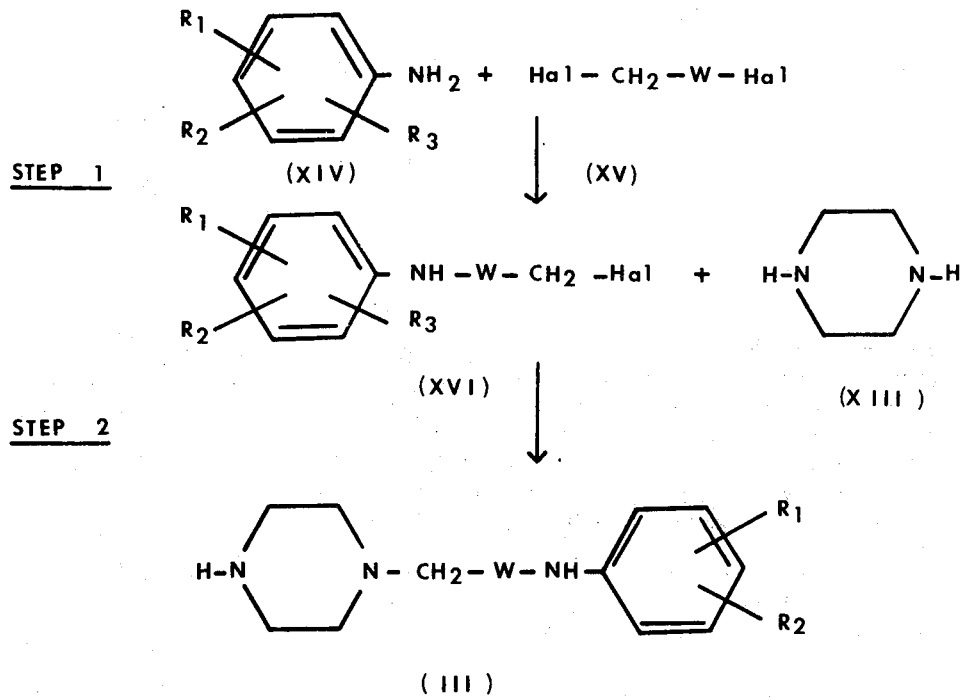

Alternatively, the piperazino-anilide compound may be obtained by a process involving the following steps:

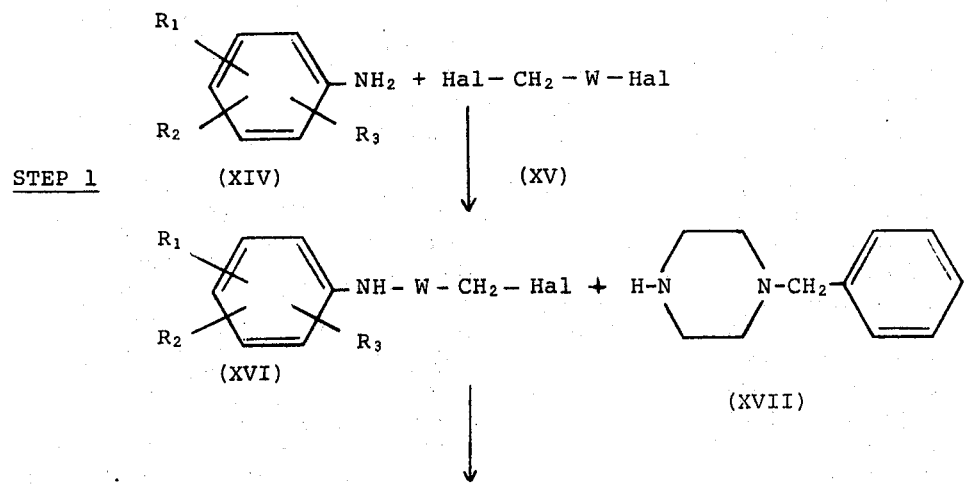

STEP 2

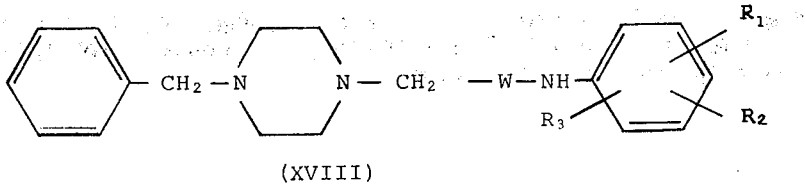

(XVIII)

STEP 3 (Debenzylation)

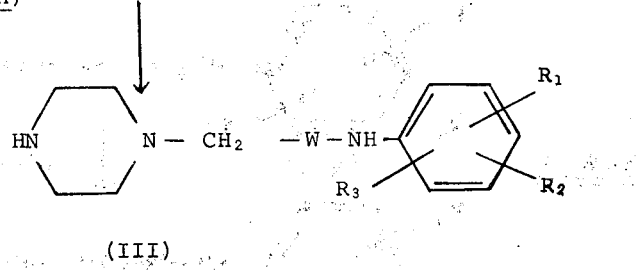

(III)

The benzyl blocking group in the compound of formula (XVIII) is removed in Step 3 using any conventional debenzylation method such as, for example, reaction with hydrogen activated by a suitable catalyst, for example, palladium-on-charcoal, in an alcoholic solvent such as methanol or ethanol. Instead of the benzyl blocking group, other blocking groups known in the art may be used.

In all the foregoing formulae in the flow sheets identified as Route A and Route B, $R_1$, $R_2$, $R_3$, W, $m$, and Hal have the same significance as hereinbefore.

DESCRIPTION OF ILLUSTRATIVE EMBODIMENTS OF ASPECTS (a) (b) and (c)

The following Examples are provided by way of illustrating the preparation of four representative compounds of the present invention. In these Examples, the melting point data was obtained by the capillary tube method.

EXAMPLE 1

1-[4'-Hydroxy-4',4'-bis-(4''-fluorophenyl)]-butyl-4-piperazinoacetyl-2,6-dimethylanilide A mixture of 9.42 g. (0.38 mole) of N-piperazinoacetyl-2,6-dimethylanilide, 11.3 g. (0.038 mole) of 1,1-bis-(4'-fluorophenyl)-4-chlorobutan-1-ol, 12.11 g. (0.114 mole) of sodium carbonate and a few crystals of iodine in 250 mls. of butyl acetate was refluxed for 18 hours. The mixture was cooled to 60°C. internal temperature and the inorganic solids filtered off. 10% hydrochloric acid was added to the filtrate until an acidic pH was obtained. The off-white precipitate was filtered off, dissolved in methanol, the solution basified with sodium hydroxide solution and the suspension extracted with chloroform. The chloroform extracts were washed with water, dried and the chloroform distilled off. Ether was added to the residue and the resultant suspension was filtered to give the desired product as an off-white solid m.p.: 173°–177°C. An analysis sample was crystallized from ethanol.

Melting Point: 177° to 180°C.

Elementary analysis

| | | C(%) | H(%) | N(%) |
|---|---|---|---|---|
| $C_{30}H_{35}F_2N_3O_2$ | Calculated: | 70.98 | 6.95 | 8.28 |
| | Found: | 70.84 | 7.20 | 8.20 |

The N-piperazinoacetyl-2,6-dimethyl-anilide starting compound was prepared as follows:

Part A

N-(2-chloracetyl)-2,6-dimethylanilide 22.58 g. (0.2 mole) of chloracetyl chloride was added slowly to a solution of 24.24 g. (0.2 mole) of 2,6-dimethylaniline and 20.23 g. (0.2 mole) of triethylamine in 600 mls. of ethylene dichloride, the temperature being maintained at 0°C. throughout the addition. The mixture was stirred for a further one hour at room temperature. 500 Mls. of water were added, the organic phase separated, washed again with water, dried, and the ethylene chloride distilled off. The residue was suspended in 150 mls. of ether and the solid filtered off to give 32.6 g. of the desired product as an off-white solid.
(m.p.: 144°–147°C.).

Part B

1-Benzyl-4-piperazinoacetyl-2,6-dimethylanilide.

A mixture of 29.5 g. (0.167 mole) of 1-benzylpiperazine, 33.09 g. (0.167 mole) of N-(2-chloroacetyl)-2,6-dimethylanilide, 53.22 g. (0.5 mole) of sodium carbonate and 0.1 g. of iodine in 580 mls. of ethyl acetate was refluxed for 18 hours and then cooled to 60°C. internal temperature. The inorganic solids were filtered off, the ethyl acetate filtrate was cooled to 0°–5°C. and stirred at this temperature for one hour. The solid was filtered off and dried to give 44.7 g. of the desired product was an off-white solid (m.p.: 146°–148°C.). The mother liquors were washed with water, dried and hydrogen chloride gas was introduced with cooling until an acidic pH was obtained. The resultant solid was filtered off, dissolved in water and the solution basified wit sodium hydroxide solution. Filtration gave a further 6.8 g. of the desired product, (m.p.: 145°–147°C.).

Part C

N-piperazinoacetyl-2,6-dimethylanilide

A solution of 13 g. of 1-benzyl-4-piperazinoacetyl-2,6-dimethylanilide in 175 mls. of methanol was hydrogenated over 1.3 g. of 5% palladium on charcoal at 45 p.s.i. at 50°C. until no more hydrogen was absorbed. The catalyst was removed by filtration and the methanol was distilled off. The residue was suspended in 50 mls. of hexane and the solid was filtered off and dried giving 9.25 g. of the desired product as a white solid (m.p. 116°–119°C.).

An analysis sample was crystallized from benzene: m.p. 117° to 119°C.

| Elementary analysis: | | C(%) | H(%) | N(%) |
| --- | --- | --- | --- | --- |
| | Calculated: | 67.98 | 8.56 | 16.99 |
| $C_{14}H_{21}N_3O$ | | | | |
| | Found: | 68.08 | 8.49 | 16.73 |

In an alternative procedure, the N-piperazinoacetyl-2,6-dimethylanilide was prepared as follows:

A solution of 15.5 g. (0.18 mole) of piperazine and 5.93 g. (0.03 mole) of N-(2-chloroacetyl)-2,6-dimethylanilide in 40 mls. of isopropanol was heated at reflux for 18 hours. The isopropanol was distilled off and the residue partitioned between chloroform and water. The chloroform phase was washed several times with water, dried and the chloroform distilled off. The residue was crystallized from benzene to give 4.9 g. of the desired product as a white solid (m.p.: 112°–116°C.).

The 1,1-bis-(4'-fluorophenyl)-4-chlorobutan-1-ol starting compound was prepared as follows:

Part A

γ-chloro-4-fluorobutyrophenone

A solution of 7.05 g. (0.05 mole) of 4-chlorobutyryl chloride in 7.69 g. (0.08 mole) of fluorobenzene was added over 30 minutes to a suspension of 7.06 g. (0.053 mole) of anhydrous aluminum chloride in 38.4 g. (0.4 mole) of fluorobenzene maintained at 15°–20°C. The resultant solution was stirred at room temperature for 30 minutes and poured slowly into ice water. The organic phase was separated, dried and the excess fluorobenzene distilled off at atmospheric pressure. The residue was distilled under reduced pressure to give 8.4 g. of a pale yellow mobile oil. b.p.: 97°–102°c./1mm Hg.

Part B 1,1-bis-(4'-fluorophenyl)-4-chlorobutan-1-ol

A Grignard reagent was prepared from 7.7 g. (0.044 mole) of 4-bromofluorobenzene, 1.07 g. of magnesium turnings and 80 mls. of anhydrous ether. The suspension was refluxed for 3 hours and to it was added slowly, maintaining a gentle reflux, a solution of 8.02 g. (0.04 mole) of γ-chloro-4-fluorobutyrophenone in 20 ml. of anhydrous ether. The resultant suspension was refluxed for 2.½ hrs., cooled at room temperature and decomposed by 200 mls. of a 10% aqueous ammonium chloride solution. The organic phase was separated, washed with water, dried and the ether distilled off to leave 11.3 g. of a pale yellow oil which was used as such for the final condensation.

EXAMPLE 2

1-[4'-Hydroxy-4',4'-bis-(4''-fluorophenyl)]-butyl-4-piperazinoacetyl-2,6-dimethylanilide dihydrochloride The purified free base obtained following the procedure set forth in Example 1 was dissolved in hot methanol and the solution acidified with gaseous hydrogen chloride (pH2—3). On cooling, the dihydrochloride salt crystallized. It was recovered by filtration and dried at 60°C. (melting point: 254° to 257°C.).

EXAMPLE 3

1-[4'-Hydroxy-4'-(4''-fluorophenyl)-4'-phenyl]-butyl-4-piperazinoacetyl-2,6-dimethylanilide This compound was prepared following a similar procedure to that set forth in Example 1 hereinbefore, by reacting together 1-phenyl-1-(4'-fluorophenyl)-4-chlorobutan-1-ol, itself prepared in a similar manner to the corresponding difluoro compound, and N-piperazino-2,6-dimethyl-anilide.

An analysis sample was crystallized from ethanol. Melting point: 174°–177°C.

| Elementary analysis: | | C(%) | H(%) | N(%) |
| --- | --- | --- | --- | --- |
| | Calculated: | 73.59 | 7.41 | 8.59 |
| $C_{30}H_{36}FN_3O_2$ | | | | |
| | Found: | 73.54 | 7.27 | 8.71 |

EXAMPLE 4

1-[4'-Hydroxy-4'-(4''-fluorophenyl)-4'-phenyl]-butyl-4-piperazinoacetyl-2,6-dimethylanilide dihydrochloride The purified free base obtained following the procedure set forth in Example 3 was converted into the dihydrochloride salt following the procedure set forth in Example 2 (melting point: 260° to 263°C.).

Although the preparation of only four specific compounds has been described in the foregoing illustrative Examples, it will be readily understood that other compounds falling within the scope of the general formula I may be obtained following similar procedures. Among such compounds, mention may be made of the following:

1-[4'-hydroxy-4',4'-bis-(4''-fluorophenyl)]-butyl-4-piperazinoacetanilide, and acid addition salts thereof;

1-[4'-hydroxy-4'-(4''-fluorophenyl)-4'phenyl]-butyl-4-piperazinoacetanilide, and acid addition salts thereof;

1-[4'-hydroxy-4',4'-bis-(4''-fluorophenyl)]-butyl-4-piperazinoacetyl-4-methylanilide, and acid addition salts thereof;

1-[4'-hydroxy-4'-(4''-fluorophenyl)-4'-phenyl]-butyl-4-piperazinoacetyl-4-methylanilide, and acid addition salts thereof;

1-[4'-hydroxy-4',4'-bis-(4''-fluorophenyl)]-butyl-4-piperazinoacetyl-2-chloro-6-methylanilide, and acid addition salts thereof;

1-[4'-hydroxy-4'-(4''-fluorophenyl)-4'-phenyl]-butyl-4-piperazinoacetyl-2-chloro-6-methylanilide, and acid addition salts thereof; 1-[4'-hydroxy-4',4'-bis/-(4''-fluorophenyl)]-butyl-4-piperazino-acetyl-4-methoxyanilide, and acid addition salts thereof;

1-[4'-hydroxy-4'-(4''-fluorophenyl)-4'-phenyl]-butyl-4-piperazinoacetyl-4-methoxyanilide, and acid addition salts thereof;

1-[4'-hydroxy-4',4'-bis-(4''-fluorophenyl)]-butyl-4-piperazino-acetyl-3,4,5-trimethoxyanilide, and acid addition salts thereof;

1-[4'-hydroxy-4'-(4''-fluorophenyl)-4'-phenyl]-butyl-4-piperazinoacetyl-3,4,5-trimethoxyanilide, and acid addition salts thereof.

1-[4'-hydroxy-4',4'-bis-(4''-fluorophenyl)]-butyl-4-piperazino-acetyl-3,4-dichloroanilide, and acid addition salts thereof:

1-[4'-hydroxy-4'-(4''-fluorophenyl)-4'-phenyl]-butyl-4-piperazinoacetyl-3,4-dichloroanilide, and acid addition salts thereof;

1-[4'hydroxy-4',4'-bis-(4''-fluorophenyl)]-butyl-4-piperazinoethyl-B-2,6-dimethylaniline, and acid addition salts thereof; and 1-[4'-hydroxy-4'-(4''-fluorophenyl)-4'-phenyl]-butyl-4-piperazinoethyl-B-2,6-dimethylaniline and acid addition salts thereof.

DESCRIPTION OF PHARMACEUTICAL COMPOSITIONS

As indicated hereinbefore, it has been found in accordance with this invention that the novel compounds of the general formula I and salts thereof have interesting biological properties in that such compounds when subjected to standard pharmacological evaluation exhibit significant coronary vasodilatory properties. Compounds acting in this way may be expected to be of use in the treatment of coronary vascular disease.

Accordingly, this invention further provides, in another of its composition of matter aspects, a pharmaceutical composition comprising as an essential ingredient at least one active compound of the general formula I or a pharmaceutically acceptable salt thereof in association with a pharmaceutically acceptable carrier therefor.

The compositions of the present invention are preferably administered either orally, parenterally or rectally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage unit form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier therefor, the quantity of the active ingredient being such that one or more units are normally required for a single therapeutic administration or that, in the case of severable units such as scored tablets, at least one fraction such as a half or a quarter of a severable unit is required for a single therapeutic administration.

The actual percentage of the active component in the composition may be varied, but advantageously is between about 2 and about 60 percent, or more, based on the total weight of the composition. Conveniently, the composition of the invention when in dosage unit form contains 0.5 mg. to 1000 mg., and more conveniently form 5 mg. to 250 mg., of the active ingredient of the general formula I.

The compositions of the present invention will normally consist of at least one compound of formula I, typically in the form of an acid addition, say, hydrochloride or maleate salt thereof admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syrup B.P., methyl cellulose, polyoxethylene sorbitan monolaurate, methyl and propyl hydroxybenzoates, pyrogen-free water and substantially isotonic saline solution. The choice of carrier is determined by the preferred form of administration, the solubility of the compound and standard pharmaceutical practice, all as more clearly set forth in "Remington's Practice of Pharmacy" by E. W. Martin and E. F. Cook, a well-known reference text in this field.

In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols (Carbowaxes) of suitable molecular weight.

The pharmaceutical compositions of this invention may contain, in addition to the active ingredient of the general formula I (or a salt thereof), one or more other pharmacologically active ingredients which elicit desirable complementary effects.

Two examples of suitable pharmaceutical compositions according to this invention are presented below for the purpose of facilitating a better understanding of this aspect of the invention.

EXAMPLE A

For oral administration, sugar coated tablets of the following composition were prepared following standard pharmaceutical practice.

| Formulation: Ingredient | Content (mg.) |
| --- | --- |
| 1-[4-Hydroxy-4',4'-bis-(4''-fluorophenyl]-butyl-4-piperazinoacetyl-2,6-dimethylanilide | 25 |
| Lactose | 60 |
| Starch | 50 |
| Sugar | 75 |
| Talc | 5 |
| Gum arabic | 5 |

EXAMPLE B

Capsules were made by the procedure described below from a mixture of the following ingredients:

| Formulation: Ingredient | Content (gms.) |
| --- | --- |
| 1-[4'-Hydroxy-4',4'-bis-(4''-fluorophenyl)]-butyl-4-piperazinoacetyl-2,6-dimethylanilide | 100 |
| Calcium phosphate | 20 |

PROCEDURE

The two ingredients were thoroughly mixed together and filled into hard gelatin capsules so that each capsule contained 50 mg. of the active ingredient.

In the foregoing Examples A and B, the active ingredient specified may be wholly or partly replaced by another pharmacologically active compound of this invention.

While in the foregoing specification various embodiments of this invention have been set forth and specific details elaborated upon for the purpose of illustration, it will be apparent to those skilled in the art that this invention is susceptible to other embodiments and that many of the details may be varied widely without departing from the spirit and scope of the invention as defined in the appended claims.

What is claimed is:

1. A 1,4-disubstituted piperazine compound having the formula:

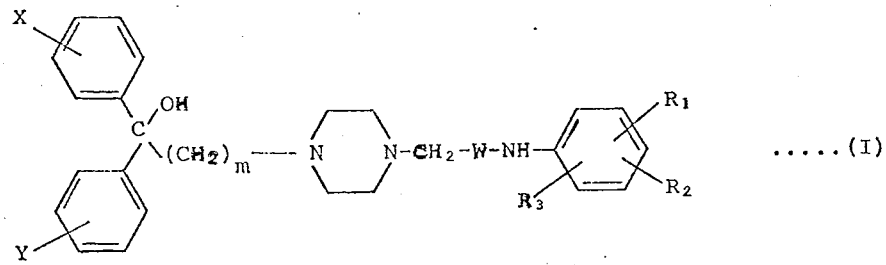

wherein X or Y is a halogen and the other is hydrogen or halogen, $R_1$, $R_2$ and $R_3$ are hydrogen, halogen, alkyl having 1 to 3 carbon atoms or alkoxy having 1 to 3 carbon atoms, W is carbonyl or methylene, and $m$ is 1, 2 or 3; or a non-toxic acid addition salt thereof.

2. A compound according to claim 1 wherein X or Y is fluorine and the other is hydrogen or fluorine, W is methylene and m is 3.

3. 1-[4′-Hydroxy-4′,4′-bis-(4″-fluorophenyl)]-butyl-4-piperazinoethyl-β-2,6-dimethylaniline as claimed in claim 2 or a non-toxic acid addition salt thereof.

4. A compound as claimed in claim 1 having the formula:

wherein X′ or Y′ is fluorine and the other is hydrogen or fluorine, $R_1$, $R_2$ and $R_3$ are hydrogen atom, halogen, alkyl having 1 to 3 carbon atoms or alkoxy having 1 to 3 carbon atoms; or a non-toxic acid addition salt thereof.

5. 1-[4′-Hydroxy-4′,4′-bis-(4″-fluorophenyl)]-butyl-4-piperazinoacetyl-2,6-dimethylanilide as claimed in claim 4 or a non-toxic acid addition salt thereof.

6. 1-[4′-Hydroxy-4′-(4″-fluorophenyl)-4′-phenyl]-butyl-4-piperazinoacetyl-2,6-dimethylanilide as claimed in claim 4 or a or a non-toxic acid addition salt thereof.

7. 1-[4′-Hydroxy-4′,4′-bis(4″-fluorophenyl)]-butyl-4-piperazinoacetanilide as claimed in claim 4 or a non-toxic acid addition salt thereof.

8. 1-[4′-Hydroxy-4′,4′-bis-(4″-fluorophenyl)]-butyl-4-piperazinoacetyl-4-methylanilide as claimed in claim 4 or a non-toxic acid addition salt thereof.

9. 1-[4′-Hydroxy-4′,4′-bis-(4″-fluorophenyl)]-butyl-4-piperazinoacetyl-2-chloro-6-methylanilide as claimed in claim 4 or a non-toxic acid addition salt thereof.

10. 1-[4′-Hydroxy-4′,4′-bis-(4″-fluorophenyl)]-butyl-4-piperazinoacetyl-4-methoxyanilide as claimed in claim 4 or a non-toxic acid addition salt thereof.

11. 1-[4′-Hydroxy-4′,4′-bis-(4″-fluorophenyl)]-butyl-4-piperazinoacetyl-3,4-dichloroanilide as claimed in claim 4 or a non-toxic acid addition salt thereof.

12. 1-[4′-Hydroxy-4′,4′-bis-(4″-fluorophenyl)]-butyl-4-piperazinoacetyl-3,4,5-trimethoxyanilide as claimed in claim 4 or a non-toxic acid addition salt thereof.

* * * * *